United States Patent [19]

Scharpf et al.

[11] 4,415,748

[45] Nov. 15, 1983

[54] INTERMEDIATES FOR INSECTICIDAL SYNTHETIC PYRETHROIDS

[75] Inventors: William G. Scharpf, Yardley; Michael S. Glenn, Langhorne, both of Pa.

[73] Assignee: FMC Corporation, Philadelphia, Pa.

[21] Appl. No.: 290,557

[22] Filed: Aug. 6, 1981

[51] Int. Cl.³ ............................................. C07C 69/63
[52] U.S. Cl. .................................... 560/227; 560/124; 560/221
[58] Field of Search ........................................ 560/227

[56] References Cited

U.S. PATENT DOCUMENTS

| 4,183,948 | 1/1980 | Huff | 424/304 |
|---|---|---|---|
| 4,235,927 | 11/1980 | Engel | 424/285 |
| 4,243,677 | 1/1981 | Engel | 424/305 |
| 4,258,202 | 3/1981 | Piccardi | 560/124 |
| 4,263,319 | 4/1981 | Engel | 560/124 |

Primary Examiner—Michael L. Shippen
Attorney, Agent, or Firm—Robert M. Kennedy; H. Robinson Ertelt; Robert L. Andersen

[57] ABSTRACT

Intermediates and Process For Insecticidal Synthetic Pyrethroids Compounds of the formulas

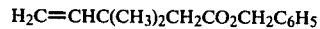

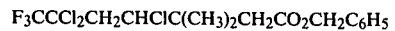

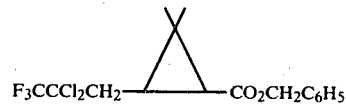

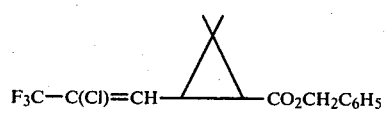

and their use in a process for preparing a pyrethroid insecticide of the formula

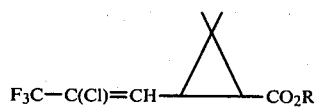

wherein R is a substituted or unsubstituted biphenylmethyl radical or 4-phenyl-2-indanyl radical are disclosed and exemplified.

1 Claim, No Drawings

INTERMEDIATES FOR INSECTICIDAL SYNTHETIC PYRETHROIDS

The present invention relates to compounds useful for preparing insecticidal esters of perhaloalkylvinylcyclopropanecarboxylic acids, and to a process employing the compounds.

U.S. Pat. No. 4,238,505, issued Dec. 9, 1980, incorporated herein by reference, discloses insecticidal substituted and unsubstituted biphenylmethyl perhaloalkylvinylcyclopropanecarboxylates, and exemplifies preparation of these compounds by esterification of the perhaloalkylvinylcyclopropanecarboxylic acid with the appropriate biphenylmethyl alcohol, via the acid chloride, and by reaction of a salt of the perhaloalkylvinylcyclopropanecarboxylic acid with the appropriate biphenylmethyl bromide.

U.S. Pat. No. 4,263,319, issued Apr. 21, 1981, incorporated herein by reference, discloses insecticidal 4-substituted-2-indanyl perhaloalkylvinylcyclopropanecarboxylates, and exemplifies preparation of 4-phenyl-2-indanyl 3-(2-chloro-3,3,3-trifluoro-1-propenyl)-2,2-dimethylcyclopropanecarboxylate by esterification of the cyclopropanecarboxylic acid with 4-phenyl-2-indanol, via the acid chloride.

The present invention provides novel intermediates for preparing various insecticidal 3-(2-chloro-3,3,3-trifluoro-1-propenyl)-2,2-dimethylcyclopropanecarboxylates, including those such compounds disclosed in the foregoing two patents.

The compounds and process of this invention have general utility for the preparation of insecticidal compounds of formula I:

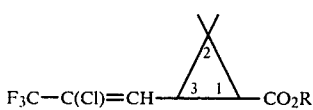

wherein R is the residue of an alcohol ROH, which alcohol forms an insecticidal ester when combined with 3-(2-chloro-3,3,3-trifluoro-1-propenyl)-2,2-dimethylcyclopropanecarboxylic acid and which alcohol is in the liquid state under a combination of temperature, pressure, and atmosphere conditions under which benzyl alcohol would be in the gaseous state, i.e., benzyl alcohol could be removed from a mixture of benzyl alcohol and ROH by distillation.

In particular, the compounds and process of this invention may be used to prepare the highly insecticidal compounds of formula I wherein R is an alcohol residue of the formula

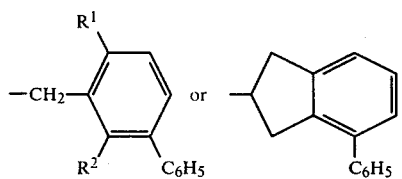

in which $R^1$ and $R^2$ are independently selected from hydrogen, halogen, and alkyl of 1 to 4 carbon atoms. Compounds of formula I of especial interest, and for the production of which the present process and compounds find specific applicability, are the biphenylmethyl compounds wherein $R^1$ is hydrogen or methyl and $R^2$ is methyl.

The compounds of this invention are the benzyl esters of formulas II, III, IV, and V:

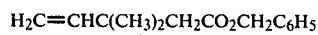   II

   III

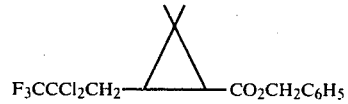   IV

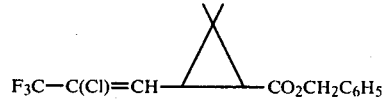   V wherein the C-1 and C-3 substituents on the cyclopropane ring in compounds IV and V are cis or trans with respect to each other or compounds IV and V are mixtures of the cis and trans isomers, and the trifluoromethyl substituent on the vinyl group of compound V has either the E or Z configuration relative to the cyclopropane ring or compound V is a mixture of the E and Z isomers.

The compounds of this invention and compound I may be prepared by the process illustrated in the following schemata, each step or combination of sequential steps of which comprises a process aspect of the present invention.

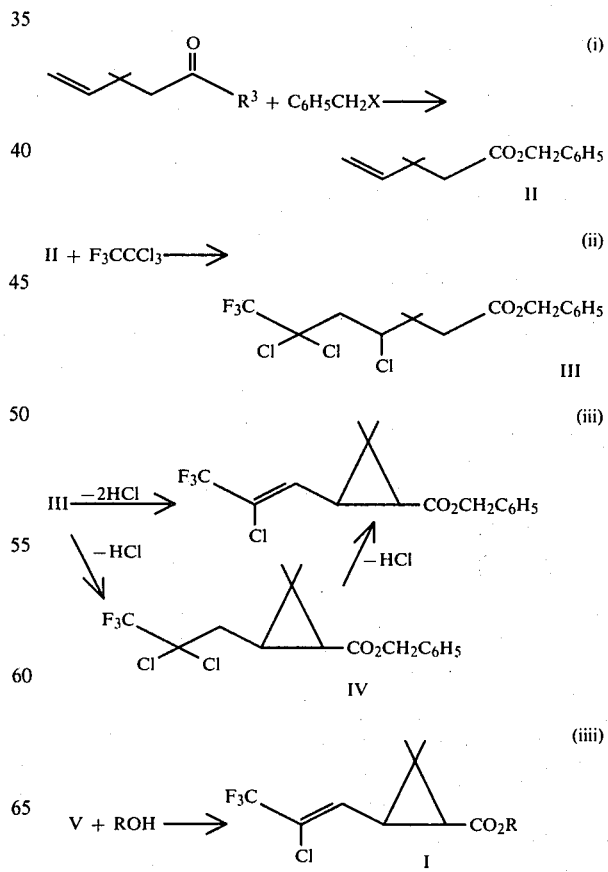

The stereochemistry of the acid portion of compound I prepared by this process will generally be similar to that of compound V.

Step (i) of the process, to produce benzyl 3,3-dimethyl-4-pentenoate, II, is, in effect, an esterification step. The reaction may be a simple dehydrative coupling of 3,3-dimethyl-4-pentenoic acid (DPA) and benzyl alcohol ($R^3$ and X are both hydroxy); a classical esterification wherein $R^3$ is an appropriate leaving group, for example, a halogen atom such as a chlorine atom or an acyloxy group such as acetoxy or 3,3-dimethyl-4-pentenoyloxy, and X is a hydroxy group; a transesterification wherein $R^3$ is an alkoxy group of 1 to 4 carbon atoms, for example, methoxy or ethoxy, and X is a hydroxy group; or a nucleophilic substitution wherein $R^3$ is an oxygen atom ionically bonded to an alkali metal such as sodium or potassium, i.e., the DPA reactant is in the form of an alkali metal salt, and X is a good leaving group, for example, a chlorine or bromine atom, a methanesulfonyloxy group, or a P-toluenesulfonyloxy group, advantageously a bromine atom.

The dehydrative type esterification reaction is conducted in the presence of a dehydrating agent, for example, dicyclohexylcarbodiimide, preferably in a solvent such as diethyl ether or tetrahydrofuran. The classical esterification reaction is preferably conducted in the presence of an inert solvent and an acid acceptor such as an amine, for example, pyridine, or any other base commonly employed as an acid acceptor in reactions of this type. The transesterification reaction of step (i) is conducted in the presence of a transesterification catalyst, for example, a titanium alkoxide of 1 to 4 carbon atoms such as titanium isopropoxide, at a temperature of at least 120° C., and is driven to completion by removal of by-product $R^3OH$. A solvent such as xylene, mesitylene, or chlorobenzene may be used, or the reaction may simply be conducted in the presence of excess benzyl alcohol which would serve both as reactant and solvent. The substitution reaction to prepare compound II is conducted at an elevated temperature, generally in the range of 50° C. to the reflux temperature of the reaction mixture. To facilitate the reaction it is advantageous to employ a phase transfer catalyst. Suitable catalysts include N,N,N',N'-tetramethylethylenediamine, N,N,N',N'-tetramethyl-1,6-hexanediamine, 3-cyclohexylamino-1-propanesulfonic acid, tetrabutylammonium chloride, and, particularly, 1,4-diazabicyclo[2.2.2]octane (DABCO). The reaction is conducted in the presence of a solvent system selected from a polar aprotic solvent and a polar aprotic solvent in combination with a non-polar solvent. For example, acetonitrile, alone or in combination with heptane, would constitute a suitable solvent system for this reaction.

In step (ii) of the process, benzyl 3,3-dimethyl-4-pentanoate, compound II, is allowed to react with 1,1,1-trichloro-2,2,2-trifluoroethane to give benzyl 3,3-dimethyl-4,6,6-trichloro-7,7,7-trifluoroheptanoate, compound III. The reaction is preferably conducted at elevated temperature in the presence of an inert solvent, an addition catalyst, and a suitable solvating agent (co-catalyst). Useful solvents include polar organic solvents such as alkyl nitriles of 2 to 4 carbon atoms, for example, acetonitrile, and alkyl alcohols of 1 to 4 carbon atoms, for example, t-butanol. Useful solvating agents include alkanolamines, preferably ethanolamine. The addition catalyst is preferably a transition-metal-containing material, for example, metallic copper, a suitable copper salt such as cuprous chloride or cuprous cyanide, or an iron salt such as ferrous chloride. Cuprous chloride is particularly desirable. The reaction is preferably conducted at a temperature in the range of about 50° C. to the boiling point of the solvent used. To assure complete reaction of the pentenoate, the trichlorotrifluoroethane is advantageously used in about a 100% to 300% excess based on the amount of pentanoate employed. It is also advantageous to use from 0.5 to 2 moles of solvating agent per mole of pentenoate reactant. Only a catalytic amount of the catalyst need be used.

In step (iii), compound V product may be produced in two sub-steps wherein compound IV is prepared first and is then converted into compound V, or in a single step directly from compound III.

The dehydrochlorination of compound III to produce IV or V is a base induced reaction requiring at least one mole of base for each mole of hydrogen chloride to be eliminated, and is suitably conducted in an inert solvent at a temperature in the range of about −78° C. to 200° C., a temperature in the lower end of the range being preferred where compound IV is the desired product, and a temperature in the higher end of the range being preferred where compound V is the desired product. In general, use of 1–1.5 or 2 moles of base per mole of compound III, a temperature of up to about 70° C., preferably up to about 25° C., and a short reaction period, for example, up to about one hour, are conditions which combine to favor the production of mono-dehydrochlorinated product, compound IV, whereas more base (2–3 moles per mole of III), a higher temperature, and a longer reaction time (up to 24 hours or longer) combine to favor di-dehydrochlorination and the production of compound V. Of course, conditions favorable for the production of compound IV may also produce a certain amount of compound V and, possibly, one or more side-products resulting from $C_{5-4}$ mono-dehydrochlorination of $C_{5-6}$ mono-dehydrochlorination of compound III.

Suitable bases for effecting the dehydrochlorination of compound III include alkali metal alkoxides of 1 to 6 carbon atoms, alkali metal amides such as sodium amide or potassium amide, alkyl lithium compounds such as n-butyllithium, sodium hydride, 1,8-diazabicyclo[5.4.0]undec-7-ene (DBU), 1,5-diazabicyclo[4.3.0]non-5-ene (DBN), and 1,4-diazabicyclo[2.2.2]octane (DABCO). Any inert solvent or solvent mixture commonly used for this type reaction will be acceptable here, keeping in mind the solubility and stability characteristics of the base in the particular solvent. It is desirable that the base be at least partially solubilized in the solvent for facile dehydrochlorination. Useful solvents include alcohols of about 1 to 5 carbon atoms, such as ethanol or t-butanol, liquid ammonia, aliphatic hydrocarbons of 5 to 8 carbon atoms such as hexane, substituted or unsubstituted aromatic hydrocarbons of 6 to 9 carbon atoms such as benzene, toluene, xylene, or chlorobenzene, ethers of 4 to 6 carbon atoms such as diethyl ether, 1,2-dimethoxyethane, 2-methoxyethyl ether, tetrahydrofuran, or dioxane, amides such as hexamethylphosphoramide, dimethylformamide, dimethylacetamide or N-methylpyrrolidone, and dimethyl sulfoxide. Where step (iii) is to be conducted in two separate dehydrochlorination sub-steps, the first sub-step to produce compound IV is preferably carried out in the presence of (a) an ether solvent of 4 to 6 carbon atoms such as tetrahydrofuran and a base selected from sodium t-butoxide, potassium t-butoxide, sodium hydride, and n-butyllithium, particularly potassium t-butoxide, or (b) liquid ammonia solvent and sodium amide or potassium amide base.

Where one wishes to maximize production of the cis isomer of compound V relative to the trans isomer, it is preferable to conduct the conversion of compound III into compound V in two separate sub-steps, proceeding first to compound IV. The cis/trans ratio in compound V product will generally be similar to that in the precursor compound, compound IV. Conditions which combine to favor production of high cis-content compound IV are (a) a low reaction temperature, generally up to about 25° C., (b) a strong base selected from alkali metal tertiary alkoxides, for example, potassium t-butoxide, alkali metal amides such as sodium amide or potassium amide, and alkyl lithium compounds such as n-butyllithium, and (c) an inert polar solvent such as tetrahydrofuran, dimethyl sulfoxide, or liquid ammonia.

The second dehydrochlorination sub-step of step (iii) of the present process, i.e., dehydrochlorination of compound IV, may be conducted by treating the product of the first dehydrochlorination sub-step (compound IV or product mixture containing compound IV) with at least one molar equivalent of base, generally at an elevated temperature, in an inert solvent. Suitable bases and solvents include any of those described above for the dehydrochlorination of compound III. Preferred base/solvent combinations are sodium t-butoxide, potassium t-butoxide, sodium hydride, or n-butyllithium, particularly potassium t-butoxide, in tetrohydrofuran, or a strong bicyclic diaza base such as DBU, DBN, or DABCO in an inert solvent such as tetrahydrofuran, a substituted or unsubstituted aromatic hydrocarbon of 6 to 9 carbon atoms, or an aliphatic hydrocarbon of 5 to 8 carbon atoms, particularly tetrahydrofuran or toluene. Where a bicyclic diaza base is used the dehydrochlorination of IV to V may conveniently be conducted at room temperature, i.e., about 25° C.

Step (iiii) of the process involves a transesterification reaction similar to the one described for step (i). Here too, the reaction is conducted in the presence of a transesterification catalyst, for example, a titanium alkoxide of 1 to 4 carbon atoms such as titanium isopropoxide, at an elevated temperature, under transesterification conditions. In step (iiii) the displaced alcohol is benzyl alcohol, and the reaction is driven to completion by distilling the benzyl alcohol from the reaction mixture as it is formed, preferably under reduced pressure. Thus, the boiling point of by-product benzyl alcohol must be lower than the boiling point of the reactant alcohol ROH. It is advantageous to conduct the reaction in a high boiling aromatic hydrocarbon solvent.

The following examples illustrate the present process as a means by which the present compounds and compound I may be prepared.

EXAMPLE 1

Synthesis of benzyl 3,3-dimethyl-4-pentenoate

To a stirred mixture of 344.0 g (2.19 moles) of ethyl 3,3-dimethyl-4-pentenoate and 240.0 g (2.22 moles) of benzyl alcohol at 100° C. was added dropwise 3.5 mL of titanium isopropoxide. After complete addition, the reaction mixture was heated at reflux temperature for approximately 7 hours, during which by-product ethyl alcohol was removed by distillation.

The contents of the reaction vessel were subjected to distillation under reduced pressure to give 376.0 g of benzyl 3,3-dimethyl-4-pentenoate, bp 107°–112° C./0.6 mm, 99% pure by gas chromatography.

EXAMPLE 2

Synthesis of benzyl 3,3-dimethyl-4,6,6-trichloro-7,7,7-trifluoroheptanoate

A stirred solution of 375.0 g (1.72 moles) of benzyl 3,3-dimethyl-4-pentenoate, 687.0 g (3.67 moles) of 1,1,1-trichloro-2,2,2-trifluoroethane, 3.0 g (0.15 mole) of cuprous chloride, and 55.0 g (0.9 mole) of ethanolamine in 1900 mL of t-butanol was heated at reflux temperature for 2 hours, then an additional 1.0 g of cuprous chloride and 10 mL of ethanolamine were added and heating at reflux temperature was continued for an additional 5 hours. The mixture was allowed to come to room temperature and was stirred for 16 hours. An additional 1.0 g of cuprous chloride and 10 mL of ethanolamine were added, and the mixture was heated at reflux temperature for 7 hours, then allowed to cool, and was stirred at room temperature for 16 hours. An additional 1.0 g of cuprous chloride and 10 mL of ethanolamine were added, and the mixture was heated at reflux temperature for 6 hours.

The excess 1,1,1-trichloro-2,2,2-trifluoroethane was distilled from the reaction mixture to leave a liquid residue. One liter of water was added to the residue, and the mixture was stirred for 1 hour. The aqueous phase was separated and extracted with two 600 mL portions of diethyl ether. The ether extractant was combined with the organic phase, and the whole was dried over sodium sulfate and filtered. The filtrate was concentrated under reduced pressure to leave a dark oil. The oil was subjected to distillation under reduced pressure to give 641.3 g of benzyl 3,3-dimethyl-4,6,6-trichloro-7,7,7-trifluoroheptanoate, bp 135°–205° C./0.5 mm, 96% purity by gas chromatography.

A previously prepared sample of this compound was purified for microanalysis by distillation, bp 166°–168° C./0.5 mm:

Anal. Calc'd. for $C_{16}H_{18}Cl_3F_3O_2$: C 47.37, H 4.47; Found: C 47.53; H 4.30.

EXAMPLE 3

Synthesis of benzyl 3-(2-chloro-3,3,3-trifluoropropenyl)-2,2-dimethylcyclopropanecarboxylate A solution of 340.0 g (3.03 moles) of potassium t-butoxide in 925 mL of tetraydrofuran was added slowly during 2 hours to a stirred and cooled ($-20°$ C.) solution of 641.2 g (1.51 moles) of benzyl 3,3-dimethyl-4,6,6-trichloro-7,7,7-trifluoroheptanoate, from Example 2, in 1500 mL of tetrahydrofuran. After complete addition, the mixture was allowed to come to room temperature slowly, over 5 hours, with stirring, then was allowed to stand for 16 hours.

The reaction mixture was heated to reflux temperature with stirring, and a solution of 418.7 g (2.75 moles) of 1,8-diazabicyclo[5.4.0]undec-7-ene (DBU) in 500 mL of tetrahydrofuran was added during 5 hours. The mixture was allowed to cool to room temperature with stirring for 16 hours, then was reheated at reflux temperature for 7 hours, allowed to cool to room temperature with stirring for 16 hours, and reheated again at reflux temperature. An additional 82.2 g (0.54 mole) of DBU was added to the refluxing mixture during 2 hours. After complete addition, heating at reflux temperature was continued for an additional 4 hours, then 2 L of tetrahydrofuran was removed by distillation. The pot residue was cooled, and 900 mL of water followed by 500 mL of diethyl ether was added. The mixture was stirred for 10–15 minutes, and the two phases were separated. The organic phase was washed with a solution consisting of 50 mL of concentrated sulfuric acid and 300 mL of water. The washings were combined with the aqueous phase, and the whole was reduced in volume to approximately 500 mL, filtered, and the filtrate extracted with 250 mL of diethyl ether. The diethyl ether extractant was combined and the organic phase from above, and the whole was dried over anhydrous magnesium sulfate, filtered, and the filtrate concentrated under reduced pressure to give an oil residue. The oil was subjected to distillation under reduced pressure to give, in several cuts, benzyl 3-(2-chloro-3,3,3-trifluoropropenyl)-2,2-dimethylcyclopropanecarboxylate. Product from one such cut weighed 119.0 g, bp 126°–128° C./0.5 mm, and was found by gas chromatographic analysis to be 93% pure.

A previously prepared sample of this compound was submitted for microanalysis:

Anal. Calc'd. for $C_{16}H_{16}ClF_3O_2$: C 57.75, H 4.85; Found: C 57.73, H 4.88.

EXAMPLE 4

Synthesis of [1,1'-biphenyl]-3-ylmethyl 3-(2-chloro-3,3,3-trifluoropropenyl)-2,2-dimethylcyclopropanecarboxylate This compound may be prepared by a method analogous to that described in Example 1, by heating a mixture of 23.7 g (0.07 mole) of benzyl 3-(2-chloro-3,3,3-trifluoropropenyl)-2,2-dimethylcyclopropanecarboxylate, 13.2 g (0.078 mole) of [1,1'-biphenyl]-3-methanol, and 15 drops of titanium isopropoxide, and removing by-product benzyl alcohol from the reaction mixture under reduced pressure as it is formed. The crude product may be purified by column chromatography on silica gel.

We claim:
1. The compound of the formula

$F_3CCCl_2CH_2CHClC(CH_3)_2CH_2CO_2CH_2C_6H_5.$

* * * * *